US00PP21133P3

(12) United States Plant Patent
Schräder

(10) Patent No.: US PP21,133 P3
(45) Date of Patent: Jun. 29, 2010

(54) **VARIETY OF *SUTERA* PLANT NAMED 'SUMSUT 04'**

(50) Latin Name: *Sutera roth*
Varietal Denomination: Sumsut 04

(75) Inventor: Ralf Schräder, Lüdinghausen (DE)

(73) Assignee: Grünewald Veredelings B.V., 's Gravenzande (NL)

( * ) Notice: Subject to any disclaimer, the term of this patent is extended or adjusted under 35 U.S.C. 154(b) by 0 days.

(21) Appl. No.: 12/284,308

(22) Filed: Sep. 19, 2008

(65) Prior Publication Data

US 2010/0077523 P1 Mar. 25, 2010

(51) Int. Cl.
*A01H 5/00* (2006.01)

(52) U.S. Cl. ..... Plt./485

(58) Field of Classification Search ..... Plt./485
See application file for complete search history.

*Primary Examiner*—June Hwu
(74) *Attorney, Agent, or Firm*—The Webb Law Firm

(57) ABSTRACT

A new and distinct *Sutera roth* plant named 'Sumsut 04' with purple colored double flowers and a compact growth habit.

1 Drawing Sheet

Botanical classification: *Sutera roth.*

Varietal denomination: 'Sumsut 04'.

BACKGROUND OF THE INVENTION

The present invention comprises a new and distinct cultivar of *Sutera* plant known by the varietal name 'Sumsut 04'. The new variety was discovered in May of 2005 in a selected breeding program in 's Gravenzande, The Netherlands. The purpose of the breeding program was to develop double-flowering *Sutera* plants with a variety of colors. The new variety is a selection from the cross of proprietary, unpatented breeding plants. The female parent was Seedling 1-5 and the male parent was Seedling 2-64. The double-flowering characteristic of the new variety is similar to its parents, but the new variety exhibits a different flower color and a more compact growth habit when compared to both parents. The new variety was first asexually reproduced in July of 2005 by tip cuttings in 's Gravenzande, The Netherlands. The new variety has been trial and field tested and has been found to retain its distinctive characteristics and remains true to type through successive asexual propagations.

The following traits distinguish 'Sumsut 04' as a new and distinct cultivar from other *Sutera* varieties known to the breeder.

Double flowers; and

Upright and compact growth habit.

The new variety exhibits double flowers like *Sutera* variety 'Sumsut 06' (U.S. Plant patent application Ser. No. 12/284,402, applied for concurrently). However, 'Sumsut 06' has white flowers and a hanging growth habit, while 'Sumsut 04' has purple flowers and a compact growth habit. The following Table 1 provides a comparative listing of botanical characteristics of Sumsut 04' and 'Sumsut 06'.

TABLE 1

| Botanical characteristics | 'Sumsut 04' | 'Sumsut 06' |
|---|---|---|
| Petal number per inflorescence: | Average of 6 (from 5-7) | 5 |
| Pistil number per inflorescence: | Average of 3 | Average of 2 |

TABLE 1-continued

| Botanical characteristics | 'Sumsut 04' | 'Sumsut 06' |
|---|---|---|
| Number of petaloids per inflorescence: | Average of 8 (4-10) | Average of 14 (8-20) |
| Flower diameter: | 14-16 mm | 18-20 mm |
| Flower length: | 7-9 mm | 10 mm |
| Peduncle length: | 6-8 mm | 18-20 mm |
| Lobe length: | 5 mm | 8 mm |
| Lobe width: | 5 mm | 7 mm |

The following Table 2 provides a listing of botanical characteristics that distinguish 'Sumsut 04' from Sutera variety 'Sumsut 05' (U.S. Plant patent application Ser. No. 12/284,404, applied for concurrently).

TABLE 2

| Botanical characteristics | 'Sumsut 04' | 'Sumsut 05' |
|---|---|---|
| Petal number per inflorescence: | Average of 6 (from 5-7) | 5 |
| Pistil number per inflorescence: | Average of 3 | 1 |
| Number of petaloids per inflorescence: | Average of 8 (4-10) | Average of 7 (4-9) |
| Flower diameter: | 14-16 mm | 15-18 mm |

DESCRIPTION OF THE DRAWING

The accompanying photographic drawing illustrates the new variety, with the color being as nearly true as is possible with color illustrations of this type.

DESCRIPTION OF THE PLANT

Figure 1:
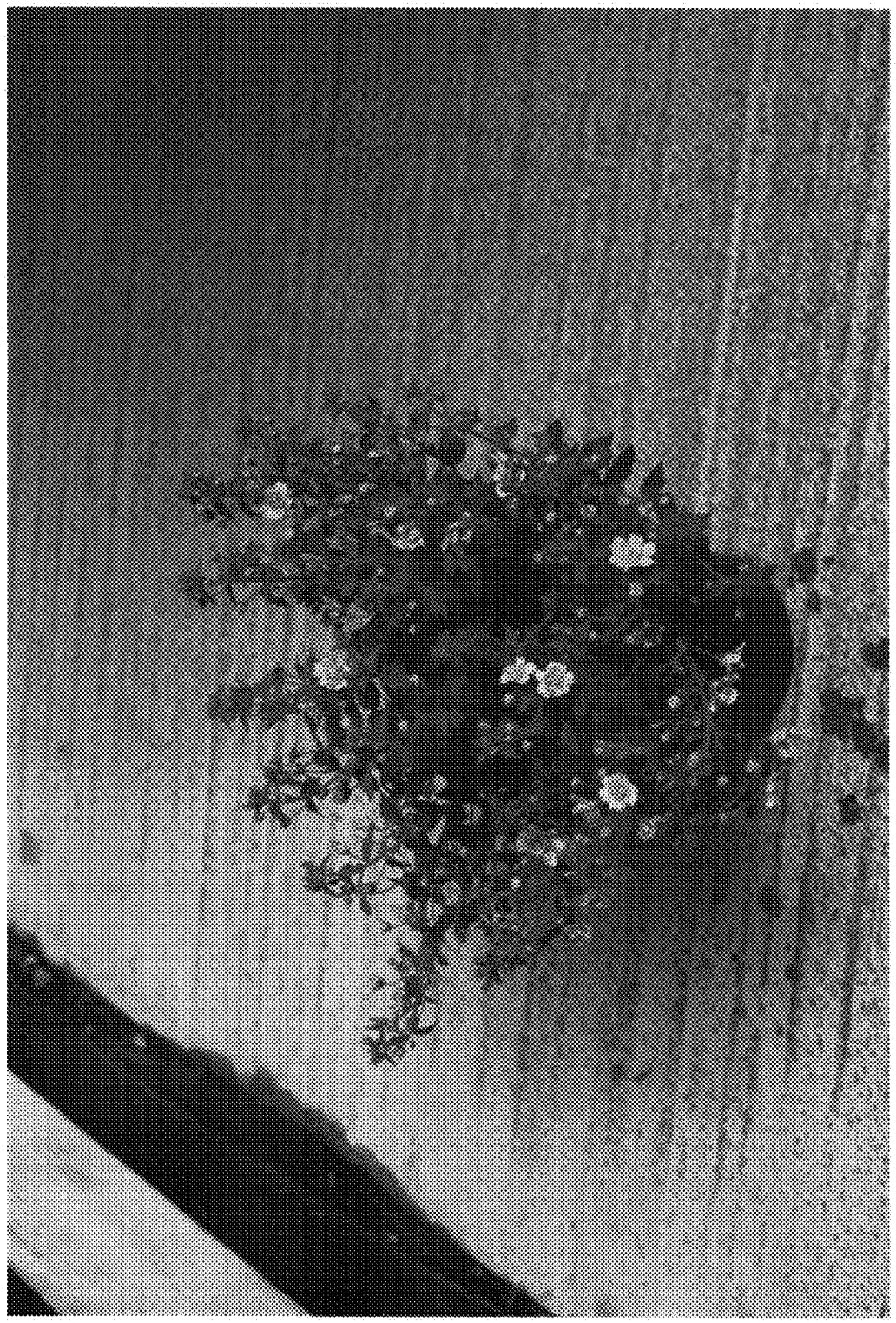
FIG. 1 is a photograph of an entire plant of the new variety.

The following detailed description sets forth the characteristics of the new cultivar. The data which defines these characteristics were collected by asexual reproductions carried out in The Netherlands. The new variety was grown in a greenhouse in a 12 cm container and was 10 weeks old when described. The color readings were taken indoors under natural light. Color references are primarily to The R.H.S. Colour Chart of The Royal Horticultural Society of London.

PLANT

Form: Mounded.
Height: Approximately 20 cm from soil to top of flowers.
Diameter: 25 cm.
Growth habit: Round and compact.
Roots:
*Habit.*—Fine and strong roots.
*Time to initiate roots.*—About 12 days at 18° C.
*Time to develop roots.*—About 21 days at 18° C.
Lateral branches:
*Form.*—Rounded.
*Color.*—146D.
*Texture.*—Smooth.
*Length.*—Approximately 12 cm.
*Diameter.*—Approximately 1 mm.
*Internode length.*—12-15 mm.
*Strength.*—High.
*Quantity.*—10-14.
Foliage:
*Arrangement.*—Opposite.
*Number of leaves per branch.*—2 per node; approximately 20-24 per branch.
*Size of leaf.*—Length: 15-17 mm. Width: 7-8 mm.
*Shape of leaf.*—Oval.
*Shape of apex.*—Acute.
*Shape of base.*—Truncate.
*Texture* (*upper and lower surfaces*).—Smooth, to the naked eye. With the aid of a magnifying glass, soft and short erect pubescence is present.
*Aspect.*—Slightly cupped.
*Margin type.*—Crenate.
*Color.*—Young leaves: Upper surface: 137C. Lower Surface: 137D. Mature leaves: Upper surface: 137C. Lower surface: 146B.
Petiole:
*Length.*—1 mm.
*Diameter.*—1 mm.
*Color.*—137C.
*Texture.*—Smooth.
Vein color: 137D on the lower surface. Veins not present on the upper surface.

FLOWER

Natural flowering season: From April to October; tolerates temperatures of about 2-38° C.
Flower type and habit: Double flowers that tilt slightly outward.
Arrangement: Raceme.
Lasting quality: Approximately 7 days.
Pest/Disease resistance or susceptibility: None observed to date.
Fragrance: None.
Flower:
*Diameter.*—Approximately 14-16 mm.
*Length.*—Approximately 7-9 mm.
*Tube diameter.*—Approximately 5 mm.
*Tube length.*—6 mm.
*Inner tube color.*—17A.
*Outer tube color.*—17D.
Petal:
*Number per inflorescence.*—Varies between 5-7; average of 6.
*Appearance.*—Weak and smooth.
*Aspect.*—Round; closed at the ground, meaning the petals are joined to each other at the base (partial corolla).
*Length.*—5 mm.
*Width.*—5 mm.
*Apex shape.*—Close to round and round.
*Margin.*—Smooth.
*Shape.*—Round.
*Texture.*—Smooth.
*Color.*—When opening: Upper surface: 197A. Lower surface: 195B. Fully opened: Upper surface: 76B. Lower surface: 76C.
Petaloids:
*Number per inflorescence.*—Varies between 4-10; average of 8.
*Shape.*—Varies and can be in regular to irregular forms. There is also a big difference in size, so the length and width measurements vary widely.
*Length.*—Varies between 3-11 mm; average of 7 mm.
*Width.*—Varies between 2-11 mm; average of 6 mm.
*Color* (*upper and lower surfaces*).—76B.
Peduncle:
*Length.*—Approximately 6-8 mm.
*Diameter.*—1 mm.
*Color.*—138A.
*Orientation.*—Outward.
*Strength.*—Very good.
*Texture.*—Smooth.
Bud:
*Shape.*—Oblanceolate.
*Length.*—Approximately 5 mm.
*Diameter.*—Approximately 3 mm.
*Color.*—157A.
Calyx:
*Appearance.*—Whorled, star-like.
*Length.*—3 mm.
*Width.*—1 mm.
*Sepals.*—Average number: 5. Apex: Needle-like. Margin: Entire. Texture: Smooth.Color: Upper surface: 143A. Lower Surface: 143A.

REPRODUCTIVE ORGANS

Stamens:
*Number.*—4.
*Filament length.*—1 mm.
*Anthers.*—Shape: Round. Length: 1 mm. Color: 7A.
*Pollen.*—Color: 7A. Amount: Slight.
Pistils:
*Average number.*—Varies between 1-5; average of 3. If there is more than one pistil per flower, then they are either totally separated from one another, or two or more of the pistils can be connected at the ovary or at the ovary and style.
*Length.*—4 mm.
*Style.*—Length: 4 mm. Color: 138B.
*Stigma.*—Shape: Oval. Color: 138B. Ovary color: 138B.
*Seeds.*—None observed to date. However, seeds could probably be produced by intensive crossing with a compatible variety.

I claim:

1. A new and distinct variety of *Sutera roth* plant substantially as shown and described herein.

* * * * *